(12) United States Patent
Kato

(10) Patent No.: US 8,472,013 B2
(45) Date of Patent: Jun. 25, 2013

(54) REFRACTIVE INDEX DISTRIBUTION MEASUREMENT METHOD AND APPARATUS THAT MEASURE TRANSMISSION WAVEFRONTS OF A TEST OBJECT IMMERSED IN DIFFERENT MEDIA HAVING REFRACTIVE INDEX LOWER THAN THAT OF THE TEST OBJECT

(75) Inventor: Seima Kato, Utsunomiya (JP)

(73) Assignee: Canon Kabushiki Kaisha (JP)

( * ) Notice: Subject to any disclaimer, the term of this patent is extended or adjusted under 35 U.S.C. 154(b) by 553 days.

(21) Appl. No.: 12/644,714

(22) Filed: Dec. 22, 2009

(65) Prior Publication Data

US 2010/0165355 A1 Jul. 1, 2010

(30) Foreign Application Priority Data

Dec. 25, 2008 (JP) ................. 2008-329274

(51) Int. Cl.
*G01N 21/41* (2006.01)
(52) U.S. Cl.
USPC ............................ 356/128; 356/124; 356/517
(58) Field of Classification Search
USPC ............ 356/517–518, 124–128, 30, 31, 73.1, 356/130
See application file for complete search history.

(56) References Cited

U.S. PATENT DOCUMENTS

| | | | |
|---|---|---|---|
| 4,265,534 A | 5/1981 | Remijan | |
| 4,541,697 A | 9/1985 | Remijan | |
| 4,542,989 A | 9/1985 | Remijan | |
| 4,565,449 A * | 1/1986 | Grego | 356/484 |
| 4,744,654 A | 5/1988 | Jinno et al. | |
| 4,934,818 A | 6/1990 | Glantschnig | |
| 5,151,752 A * | 9/1992 | Oono et al. | 356/128 |
| 5,309,214 A | 5/1994 | Hashimoto | |
| 5,526,118 A | 6/1996 | Miyagawa et al. | |
| 6,765,661 B2 | 7/2004 | Biel et al. | |

(Continued)

FOREIGN PATENT DOCUMENTS

| | | |
|---|---|---|
| JP | 58-045526 A | 3/1983 |
| JP | 61-070436 A | 4/1986 |

(Continued)

OTHER PUBLICATIONS

Takeda, Mitsuo et al., "Lateral Aberration Measurements With a Digital Talbot Interferometer" Applied Optics, vol. 23, No. 11, Jun. 1, 1984, pp. 1760-1764 (cited in related publication 2010/0245842).

(Continued)

*Primary Examiner* — Tarifur Chowdhury
*Assistant Examiner* — Michael P Lapage
(74) *Attorney, Agent, or Firm* — Rossi, Kimms & McDowell LLP

(57) ABSTRACT

A refractive index distribution measurement method includes the steps of measuring a first transmission wavefront of a test object by introducing reference light to the test object immersed in a first medium having a first refractive index lower than that of the test object by 0.01 or more, measuring a second transmission wavefront of the test object by introducing the reference light to the test object immersed in a second medium having a second refractive index lower than that of the test object by 0.01 or more and different from the first refractive index, and obtaining a refractive index distribution of the test object based on a measurement result of the first transmission wavefront and a measurement result of the second transmission wavefront.

14 Claims, 4 Drawing Sheets

U.S. PATENT DOCUMENTS

| | | |
|---|---|---|
| 7,388,676 B2 | 6/2008 | Sawada |
| 2006/0159332 A1 | 7/2006 | Sawada |
| 2007/0109555 A1 | 5/2007 | Gustafsson et al. |
| 2009/0109401 A1* | 4/2009 | Van Heugten ............... 351/221 |
| 2009/0147241 A1* | 6/2009 | Shlezinger et al. ............ 356/30 |
| 2010/0245842 A1 | 9/2010 | Kato |
| 2011/0134438 A1 | 6/2011 | Kato |
| 2011/0292379 A1 | 12/2011 | Kato |
| 2012/0139136 A1 | 6/2012 | Kato |
| 2012/0241989 A1 | 9/2012 | Sugimoto |

FOREIGN PATENT DOCUMENTS

| | | |
|---|---|---|
| JP | 1-035282 B2 | 7/1989 |
| JP | 01-316627 A | 12/1989 |
| JP | 02-008726 A | 1/1990 |
| JP | 3-128411 A | 5/1991 |
| JP | 08-304229 A | 11/1996 |
| JP | 11-044641 A | 2/1999 |
| JP | 2006-200999 A | 8/2006 |
| JP | 2010-151578 A | 7/2010 |

OTHER PUBLICATIONS

Takeda, Mitsuo et al., "Fourier-Transform Method of Fringe-Pattern Analysis for Computer-Based Topography and Interferometry" Optical Society of America, vol. 72, No. 1, Jan. 1982, pp. 156-160 (cited in related publication 2010/0245842).

KR Office Action issued Aug. 10, 2012 for corresponding KR 10-2009-0120318.

* cited by examiner

REFRACTIVE INDEX DISTRIBUTION MEASUREMENT METHOD AND APPARATUS THAT MEASURE TRANSMISSION WAVEFRONTS OF A TEST OBJECT IMMERSED IN DIFFERENT MEDIA HAVING REFRACTIVE INDEX LOWER THAN THAT OF THE TEST OBJECT

BACKGROUND OF THE INVENTION

1. Field of the Invention

The present invention relates to a method and apparatus for measuring a refractive index distribution of a test object such as an optical element.

2. Description of the Related Art

A high refractive index is required for an optical element such as a lens used for an optical unit, for example, a digital camera or a laser beam printer. An optical glass or plastic material having a high refractive index can easily be made into a complex shape of an aspheric surface or the like by using the molding technology.

However, molding may cause an uneven refractive index distribution in the optical element depending on molding conditions. The uneven internal refractive index distribution may greatly deteriorate an optical characteristic of the optical element, and a predetermined optical characteristic may not be maintained. Therefore, optical homogeneity in the optical element having a high refractive index needs to be measured with high accuracy.

A fringe measurement method is generally known as a method for measuring the optical homogeneity. The fringe measurement method highly accurately works a test object (optical element) and measures its transmission wavefront, thereby measuring its internal refractive index distribution. Another proposed method reduces a surface accuracy error of a test object by holding the test object between glass plates and by immersing the test object in oil that has a refractive index approximately equal to that of the test object and is poured between the glass plates.

Japanese Patent Laid-Open No. ("JP") 01-316627 discloses a method for obtaining an optical characteristic of a test object by immersing the test object in a medium (matching oil) having a refractive index approximately equal to that of the test object to measure a transmission wavefront. This method can obtain the internal refractive index distribution of the test object without highly accurately working the test object.

A measurement method disclosed in JP 02-008726 measures a transmission wavefront by immersing a test object in first matching oil having a refractive index approximately equal to that of the test object. The method further measures a transmission wavefront by immersing the test object in second matching oil having a refractive index slightly different from that of the test object. The method obtains a shape and a refractive index distribution of the test object from a measurement result using the first matching oil and a measurement result using the second matching oil.

In the measurement using the second matching oil, influences of the refractive index distribution and the shape of the test object appear as an interference pattern in a detector. The refractive index of the second matching oil needs to be slightly different from that of the test object to the extent that interference patterns are not excessively dense.

The measurement methods disclosed in JPs 01-316627 and 02-008726 need matching oil having a refractive index approximately equal to that of the test object. However, the matching oil of a high refractive index has a low transmittance. Thus, the measurements of the transmission wavefront of the optical element of a high refractive index by the methods disclosed in JPs 01-316627 and 02-008726 can obtain only a weak signal from the detector, and their measurement accuracies are low.

SUMMARY OF THE INVENTION

The present invention provides a measurement method and apparatus configured to highly accurately measure an internal refractive index distribution of a test object.

A refractive index distribution measurement method according to the present invention includes the steps of measuring a first transmission wavefront of a test object by introducing reference light to the test object immersed in a first medium having a first refractive index lower than that of the test object by 0.01 or more, measuring a second transmission wavefront of the test object by introducing the reference light to the test object immersed in a second medium having a second refractive index lower than that of the test object by 0.01 or more and different from the first refractive index, and obtaining a refractive index distribution of the test object based on a measurement result of the first transmission wavefront and a measurement result of the second transmission wavefront.

Further features of the present invention will become apparent from the following description of exemplary embodiments with reference to the attached drawings.

DESCRIPTION OF THE EMBODIMENTS

Figure 1:
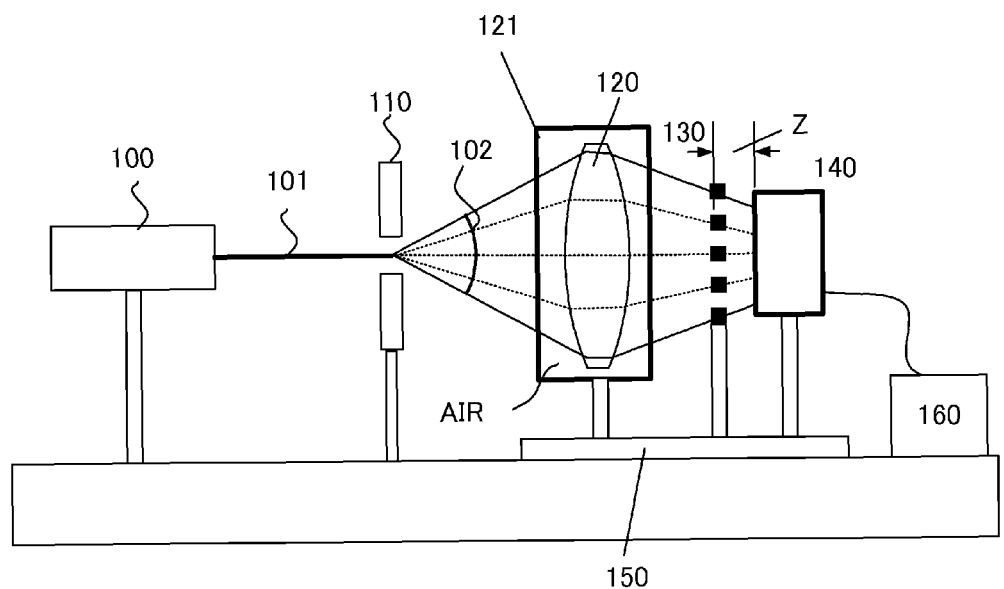
FIG. 1 shows a schematic configuration of a measurement apparatus according to a first embodiment of the present invention which uses a first medium.

Referring now to the drawings, a description will be given of embodiments according to the present invention.

First Embodiment

In this embodiment, a description will be given of a refractive index distribution measurement method for obtaining an internal refractive index distribution of a test object by immersing the test object in two types of media (air and water) and by measuring a transmission wavefront for each medium.

FIG. 1 shows a schematic configuration of a Talbot interferometer (refractive index distribution measurement apparatus) which is used when the test object is measured in the air (first medium). The test object 120 that is an optical element such as a lens is immersed in the air in a test object case 121. A refractive index of the air is lower than that of the test object 120 by 0.01 or more.

Laser light 101 emitted from a laser light source (e.g., He—Ne laser) 100 is diffracted when it passes through a pinhole (optical unit) 110. The diffracted light (reference light) 102 diffracted by the pinhole 110 passes through the air in the test object case 121, and enters and passes the test object 120 for which the pinhole 110 is an object plane. A diameter φ of the pinhole 110 is designed small enough to regard the diffracted light 102 as an ideal spherical wave and to satisfy the following equation 1 by using a numerical aperture NAO of the test object side and a wavelength λ of the laser light source 100:

$$\phi \approx \frac{\lambda}{NAO} \qquad \text{Equation 1}$$

When the wavelength λ is 600 nm and the numerical aperture NAO is about 0.3, the diameter φ of the pinhole 110 may be about 2 μm.

The laser light transmits through the test object 120 and the air in the test object case 121 and passes through an orthogonal diffraction grating 130 that is a two-dimensional diffraction grating to be captured (measured) by a CCD 140 that is a detector.

When an image side numerical aperture NA of the test object 120 is small, and a distance Z between the diffraction grating 130 and the CCD 140 satisfies the Talbot condition represented by the following equation 2, a spurious resolution of the diffraction grating 130 is obtained as an interference pattern on the CCD 140:

$$\frac{Z_0 Z}{Z_0 - Z} = \frac{md^2}{\lambda} \qquad \text{Equation 2}$$

Z denotes a distance between the diffraction grating 130 and the CCD 140, which is referred to as a Talbot distance hereinafter, m denotes an integer excluding 0, and d denotes a pitch of the diffraction grating 130. $Z_0$ denotes a distance from the diffraction grating 130 to an image plane of the test object 120. The grating pitch d of the diffraction grating 130 is determined according to a size of an aberration of the test object 120.

The laser light source 100, the pinhole 110, the diffraction grating 130, the CCD 140, and the test object case 121 (test object 120) that are components of the measurement apparatus are guided on a rail 150 laid in parallel to an optical axis of the test object 120 so that they can move relative to the test object 120 in an optical axis direction.

Figure 2:
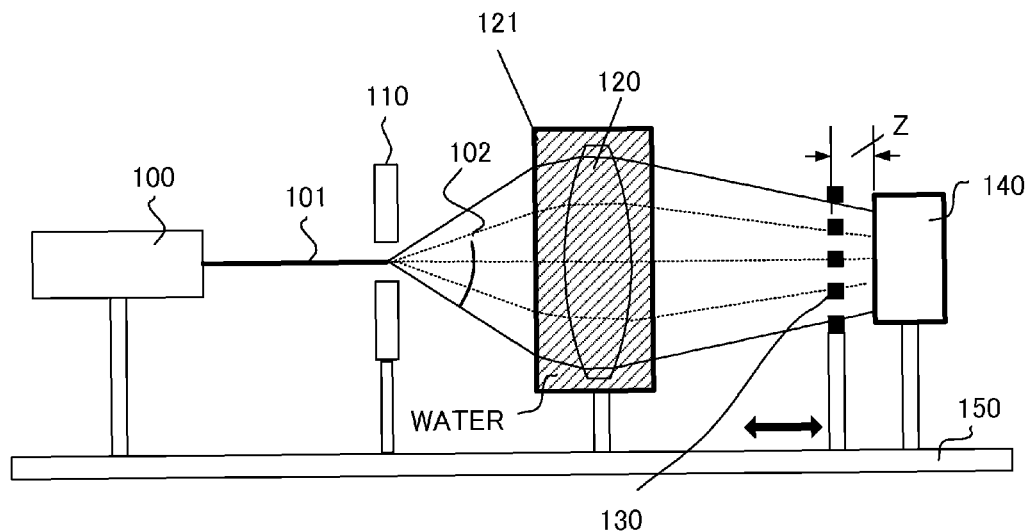
FIG. 2 shows a schematic configuration of the measurement apparatus of the first embodiment which uses a second medium.

FIG. 2 shows a schematic configuration of the Talbot interferometer when the test object 120 is measured underwater (in a second medium). The test object 120 is immersed in the water in the test object case 121. A refractive index of water is lower than that of the test object 120 by 0.01 or more and different from that of air.

The diffraction grating 130 and the CCD 140 are placed more distant from the test object 120 than those of FIG. 1 where air is used as the medium.

The laser light 101 emitted from the laser light source 100 is diffracted by the pinhole 110 and becomes diffracted light (reference light) 102, passes through water in the test object case 121, and enters and passes the test object 120 for which the pinhole 110 is the object plane. The laser light transmitted through the test object 120 and water in the test object case 121 passes through the diffraction grating 130 and captured (measured) by the CCD 140.

Figure 3:
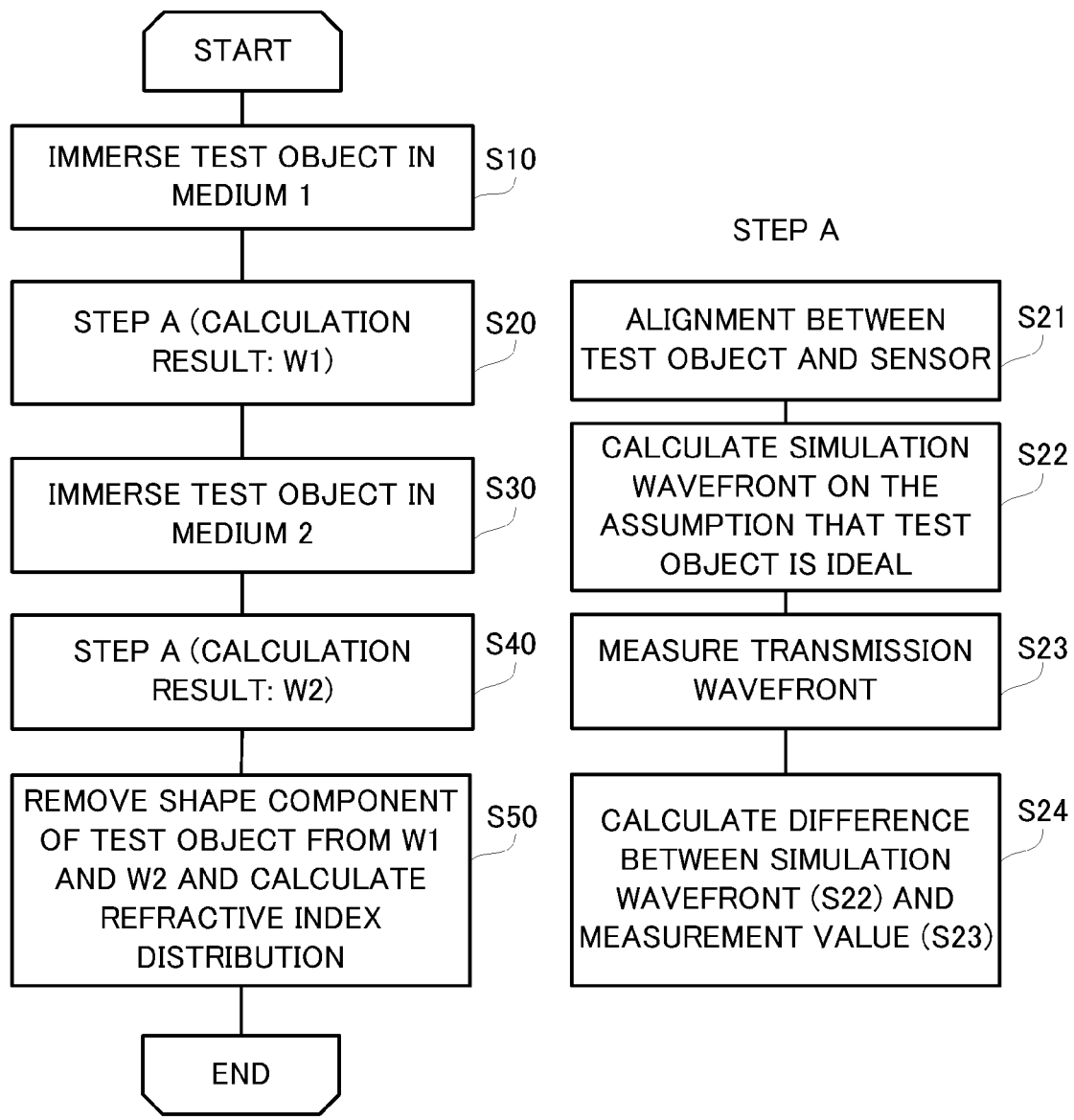
FIG. 3 is a flowchart showing a calculation procedure of an internal refractive index distribution according to the first embodiment.

FIG. 3 shows a procedure of calculating a refractive index distribution $W_{index}$ of the test object 120 by using an image taken by the CCD 140. An operation unit (calculation module), such as a microcomputer 160 shown in FIG. 1, provides this calculation according to a computer program.

First, as shown in FIG. 1, the test object 120 is placed in the test object case 121 in which air (medium 1 in FIG. 3) is filled (step S10).

Then, through step A described below, a wavefront aberration W1 when the medium in the test object case 121 is air is calculated (step S20).

The step A includes the following four sub-steps. Initially, the test object 120, the diffraction grating 130, and the CCD 140 are moved on the rail 150 to appropriate positions (sub-step S21). Hereinafter, the diffraction grating 130 and the CCD 140 will collectively be referred to as a sensor.

The image side NA is reduced by changing a distance between the pinhole 110 and the test object 120. In order to obtain the spurious resolution of the diffraction grating 130 on the entire surface of the CCD 140 using the Talbot interferometer, the numerical aperture NA needs to be reduced to about 0.3 or less. When a light receiving surface of the diffraction grating 130 or the CCD 140 is smaller than a diameter of a light flux that has transmitted through the test object 120, the sensor is separated from the test object 120 so that the light flux is maintained within the light receiving surface.

Next, a simulation wavefront $W_{sim}$ is calculated on the assumption that the test object 120 has an ideal internal refractive index distribution (specific refractive index distribution) (sub-step S22). This sub-step uses the same arrangement as that of the sub-step S21, and calculates a transmission wavefront on the assumption that an internal refractive index of the test object is uniform. A test object having such a uniform refractive index will be referred to as a reference test object. The simulation wavefront $W_{sim}$ is a transmission wavefront of the reference test object.

Figure 4:
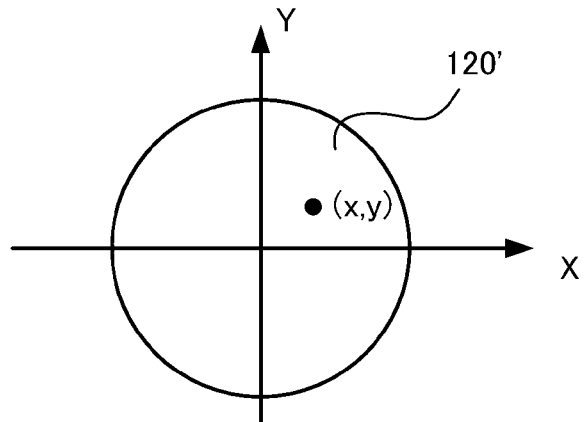
FIG. 4 shows a coordinate system defined on a test object.

A simulation wavefront $W_{sim}$ at a point (x, y) located within a reference test object 120' shown in FIG. 4 is represented by the following Equation 3:

$$W_{sim}(x,y) = L1(x,y) + L2(x,y)N_1 + L3(x,y)Ng + L4(x,y)N_1 + L5(x,y) \qquad \text{Equation 3}$$

Figure 5:
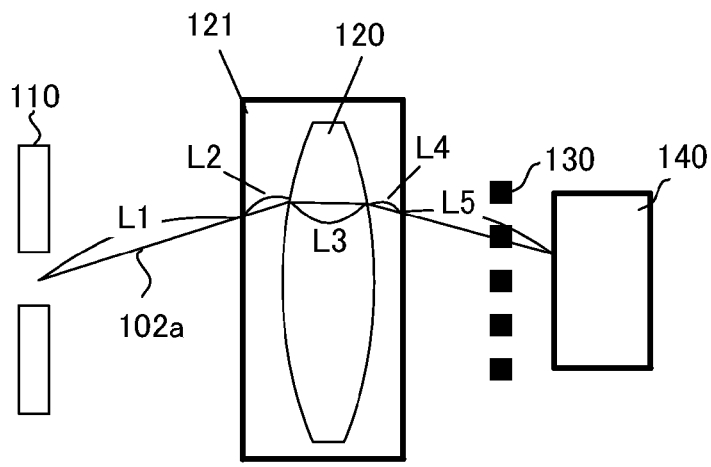
FIG. 5 shows an optical path in the measurement apparatus according to the first embodiment.

L1 to L5 denote geometrical distances between the respective components along a ray 102a shown in FIG. 5. The ray 102a passes through the point (x, y) in the test object 120' shown in FIG. 4. $N_1$ denotes a refractive index of air, and Ng denotes an ideal refractive index of the test object 120 (refractive index of the referent test object). A thickness of a wall of the test object case 121 is ignored to simplify the Equation 3.

Next, a (first) transmission wavefront $W_m$ is measured using the Talbot interferometer shown in FIG. 1 in which the test object 120 is placed in air (sub-step S23). This sub-step includes an image acquisition of an interference pattern by the CCD 140 and an image recovery of the transmission wavefront using a processing circuit (not shown). The image recovery of the transmission wavefront (also referred to as a "wavefront recovery" hereinafter) is performed by a fast Fourier transform ("FFT") method, which separates a carrier fringe from an aberration utilizing the nature of the aberration that disturbs the carrier fringe of interference patterns.

More specifically, the two-dimensional FFT is performed for the interference pattern to convert them into a frequency map. Next, only a portion close to a carrier frequency is cut out of the frequency map, a coordinate conversion is performed so that the carrier frequency can be an origin, and an inverse fast Fourier transform ("iFFT") is performed. Thus, a phase item of a complex amplitude map is obtained. The resultant phase map becomes a transmission wavefront.

A wavefront $W_m$ is represented by the following equation 4 based on the geometrical distances L1 to L5 of FIG. 5:

$$W_m(x,y) = L1(x,y) + L2(x,y)N + \{L3(x,y) + dL\}N(x,y) + \{L4(x,y) - dL\}N + L5(x,y) \qquad \text{Equation 4}$$

N(x, y) denotes a refractive index averaged in a thickness direction of the test object 120 on coordinates (x, y), and dL denotes a thickness error of the test object 120 on the coordinate (x, y).

Finally, a wavefront aberration W1 corresponding to a difference between the simulation wavefront $W_{sim}$ obtained at the sub-step S22 and the transmission wavefront $W_m$ obtained at the sub-step S23 is obtained from the following equation 5 (sub-step S24). A relationship between W1 and the refractive index distribution $W_{index}$ of the test object 120 is as follows:

$$\begin{aligned} W1 &= W_m - W_{sim} \qquad \text{Equation 5} \\ &= L3(x,y)\{N(x,y) - Ng\} + \\ &\quad dL(Ng - N_1) + dL\{N(x,y) - Ng\} \\ &\cong W_{index} + dL(Ng - N_1) \end{aligned}$$

$$W_{index} = L3(x,y)\{N(x,y) - Ng\}$$

$$dL\{N(x,y) - Ng\} \cong 0 \qquad \text{Equation 6}$$

Next, as shown in FIG. 2, the test object 120 is placed in the test object case 121 in which water has been filled (referred to as a medium 2 in FIG. 3) (step S30).

Next, a wavefront aberration W2 when the medium in the test object case 121 is water is calculated through the above step A (step S40).

More specifically, the test object 120 and the sensor are located in place (sub-step 21), and a simulation wavefront $W_{sim}$ is calculated on the assumption that the test object 120 immersed in the water has an ideal internal refractive index distribution (sub-step 22). Next, a (second) transmission wavefront $W_m$ is measured while the test object 120 is immersed in water (sub-step S23), and a wavefront aberration W2 corresponding to a difference between the simulation wavefront $W_{sim}$ and the transmission wavefront $W_m$ is obtained (sub-step S24). $N_2$ in the following equation 7 denotes a refractive index of water:

$$W2 \cong W_{index} + dL(Ng - N_2) \qquad \text{Equation 7}$$

Next, a shape component dL of the test object 120 is removed from the wavefront aberrations W1 and W2 utilizing the following equation 8, and a refractive index distribution $W_{index}$ of the test object 120 is calculated (step S50). Thus, the calculation of the refractive index distribution $W_{index}$ is completed:

$$W_{index} = \frac{(Ng - N_1)W2 - (Ng - N_2)W1}{N_2 - N_1} \qquad \text{Equation 8}$$

For example, assume Ng=1.600, $N_1$=1.000 and $N_2$=1.333 in the equation 8. Then, the refractive index distribution $W_{index}$ is represented by the following equation 9:

$$W_{index} = 1.802 W2 - 0.802 W1 \qquad \text{Equation 9}$$

A refractive index distribution $W_{index}$ is calculated without any approximations using Ng=1.600 and N(x, y)=1.601 in order to check the influence of the approximation used in the equation 6. The refractive index distribution is represented by the following equation 10:

$$W_{index} = 1.805 W2 - 0.805 W1 \qquad \text{Equation 10}$$

A difference between this refractive index distribution $W_{index}$ and the refractive index distribution $W_{index}$ obtained by the equation 9 is less than 1%, and hence the approximation of the equation 6 is permissible.

The above-mentioned calculation assumes that the geometrical optical path length L3 in the test object 120 is maintained constant when the medium is changed. In reality, however, there may be a slight difference between the geometrical length L3 at Step S20 and the geometrical length L3 at Step S40. This difference occurs because it is difficult to maintain a perfectly equal inclination of a ray that passes through the test object 120 when the medium is changed.

When a geometrical optical path length in the test object 120 in the step S40 is L3+ΔL, a difference $\Delta W_{index}$ of the refractive index distribution $W_{index}$ caused by ΔL is represented by the following equation 11:

$$\frac{\Delta W_{index}}{W_{index}} = -\frac{\Delta L}{L3} \frac{Ng - N_1}{N_2 - N_1} \qquad \text{Equation 11}$$

In order to reduce the difference $\Delta W_{index}/W_{index}$ in the equation 11, ΔL and Ng−$N_1$ may be made smaller and $N_2$−$N_1$ may be made larger. Ng denotes a refractive index of a high refractive index glass material, and this embodiment assumes that use of a medium having a refractive index equal to that of the test object is difficult. Thus, in order to reduce the difference, an inclination of a ray (a ray of the reference light) which passes through the test object may be made equal when the medium is changed and ΔL is made smaller or a difference of a refractive index between the two types of media may be made larger.

When the inclination of the ray that passes through the test object when the medium is changed is made approximately equal within about an angle of 30 seconds for the test object of L3=10 mm, ΔL becomes about 1 μm. In this case, in order to reduce a difference $\Delta W_{index}/W_{index}$ to 1% or less, the refractive indexes of the two types of media need to be different from each other by 0.01 or more.

As in this embodiment, use of the Talbot interferometer as a measurement apparatus (measuring device) enables a large aberration caused by a refractive index difference between the test object and the medium to be measured. The Talbot interferometer is one type of a lateral shearing interferometer configured to measure as an interference pattern a difference between a transmission wavefront and its laterally shifted (sheared) transmission wavefront.

Therefore, the shearing interferometer is a measurement unit configured to obtain an amount corresponding to a gradient (inclination) of a wavefront shape of the transmission wavefront. A lateral shift amount of the transmission wavefront is referred to as a shear amount, and reducing the shear amount enables a large transmission wavefront aberration to be measured as a small aberration (shear wavefront) to the extent that the interference patterns is not dense.

In general, in the shearing interferometer, when a shear amount is excessively small, a shear wavefront is buried in noise and the accuracy drops. Thus, a shear amount may be about 3 to 5% of a diameter of a pupil. In this embodiment, however, in order to measure a transmission wavefront of a large aberration by a small shear wavefront, a shear amount may be reduced to 1.5% or less, preferably about 0.4 to 0.9%.

A shear amount "shear" is defined by the following equation 12 using the Talbot distance Z and a diameter D of the interference pattern data on the CCD 140:

$$\text{shear} = \frac{\lambda Z}{dD} \qquad \text{Equation 12}$$

The equation 12 can be represented by the following equation 13 using the equation 2 and a diameter $D_0$ of a light flux on the diffraction grating 130:

$$\text{shear} = \frac{md}{D_0} \qquad \text{Equation 13}$$

It is understood from the equation 13 that the shear amount is proportional to a grating pitch of the diffraction grating 130. As understood from the equation 2, the pitch of the diffraction grating 130 affects the Talbot distance Z, and hence the pitch needs to be determined by taking into account interferences among the components of the measurement apparatus. For example, when m=1 and the diameter $D_0$ is about 10 to 20 mm, a grating pitch may be about 40 to 180 μm.

As described above, this embodiment measures the first transmission wavefront of the test object immersed in air having the first refractive index lower than that of the test object by 0.01 or more by introducing the reference light to the test object. The second transmission wavefront of the test object is measured by introducing the reference light to the test object in water having the second refractive index lower than that of the test object by 0.01 or more and different from that of air. Then, the refractive index distribution of the test object is obtained based on the measurement results of the first and second transmission wavefronts.

As a result, even when the refractive index of the test object is high, use of a medium having a refractive index lower than that of the test object provides a highly accurate measurement of the internal refractive index distribution of the test object.

While this embodiment uses air and water for the two types of media, two types of media are not limited to them as long as refractive indexes thereof are different from each other by about 0.01 or more. Two types of media may be the same material having different refractive indexes caused by different temperatures.

While this embodiment uses the Talbot interferometer, other different shearing interferometers such as a lateral shearing interferometer and a radial shearing interferometer can be used.

Second Embodiment

Figure 6:
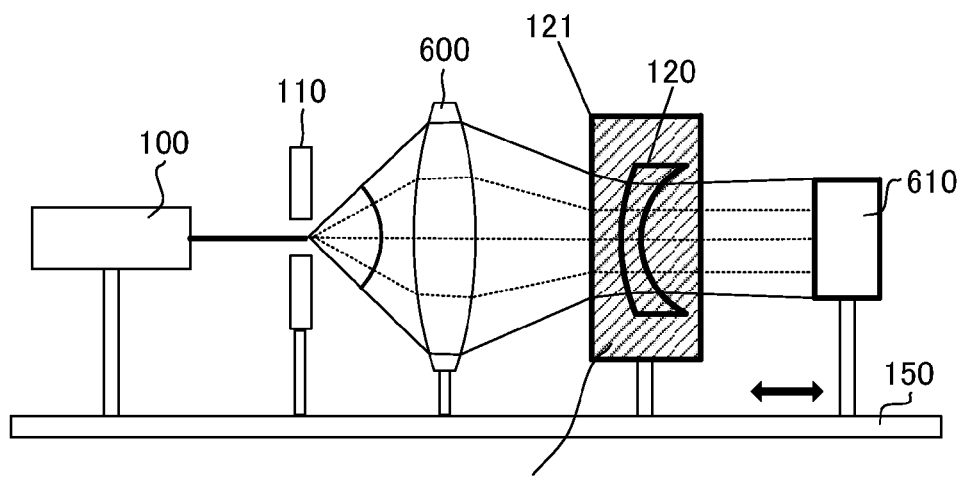
FIG. 6 is a conceptual view of a measurement apparatus according to a second embodiment of the present invention.

The second embodiment of the present invention discusses a test object 120 having a negative power and a measurement apparatus other than a shearing interferometer. FIG. 6 is a conceptual view of a measurement apparatus of this embodiment.

Figure 7:
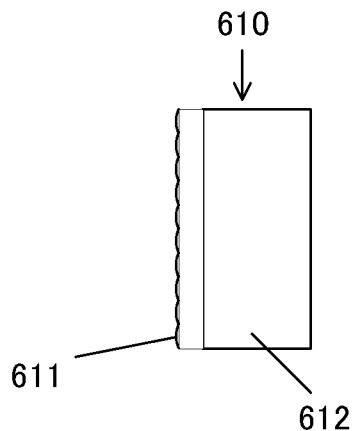
FIG. 7 is a schematic view of a Shack-Hartmann sensor for use with the second embodiment.

A pinhole 110 generates (reference) light having an ideal spherical wave by using laser light emitted from a laser light source 100. This light is converted into converged light by an illumination optical system 600. The converged light passes through the test object 120 that is a meniscus lens, and its transmission wavefront is measured by a Shack-Hartman sensor 610 that is a wavefront measurement sensor. As shown in FIG. 7, the Shack-Hartmann sensor 610 includes a lens array 611 and a CCD 612.

As the illumination optical system 600 is moved on a rail 150 in an optical axis direction of the test object 120, a light flux made incident upon the test object 120 can be turned into any one of a divergent light flux, a parallel light flux, and a converged light flux. Thus, a numerical aperture NA of the light flux made incident upon the Shack-Hartmann sensor 610 can be adjusted.

The Shack-Hartmann sensor 610 needs to control the numerical aperture NA of the incident light flux more strictly than the Talbot interferometer. However, when the Shack-Hartmann sensor 610 is used, there is no need to adjust a position of the sensor 610 to the Talbot distance, and hence the alignment of the sensor 610 becomes easier.

The Shack-Hartmann sensor 610 is configured to condense light incident upon the lens array 611 onto the CCD 612. When an inclined transmission wavefront enters the lens array 611, a light condensing point shifts. The Shack-Hartmann sensor 610 can convert the inclination of the transmission wavefront into a position of a light condensing point, measures the position, and thus can measure a wavefront having a large aberration.

Since a calculation method of an internal refractive index distribution of the test object 120 in this embodiment is similar to that of the first embodiment, a description thereof will be omitted.

Any measurement apparatuses are applicable to this embodiment of the present invention as long as it can measure an amount corresponding to a gradient of a wavefront shape of a transmission wavefront or inclination of a ray, and detects the gradient or the inclination as a measurable physical amount, even in a transmission wavefront having a large aberration. Thus, a measurement apparatus that uses the Hartmann method or the Ronchi test may be used in addition to the Shack-Hartmann method.

Third Embodiment

A measurement result of a refractive index distribution measurement method according to the present invention can be fed back to a method for manufacturing an optical element such as a lens.

Figure 8:
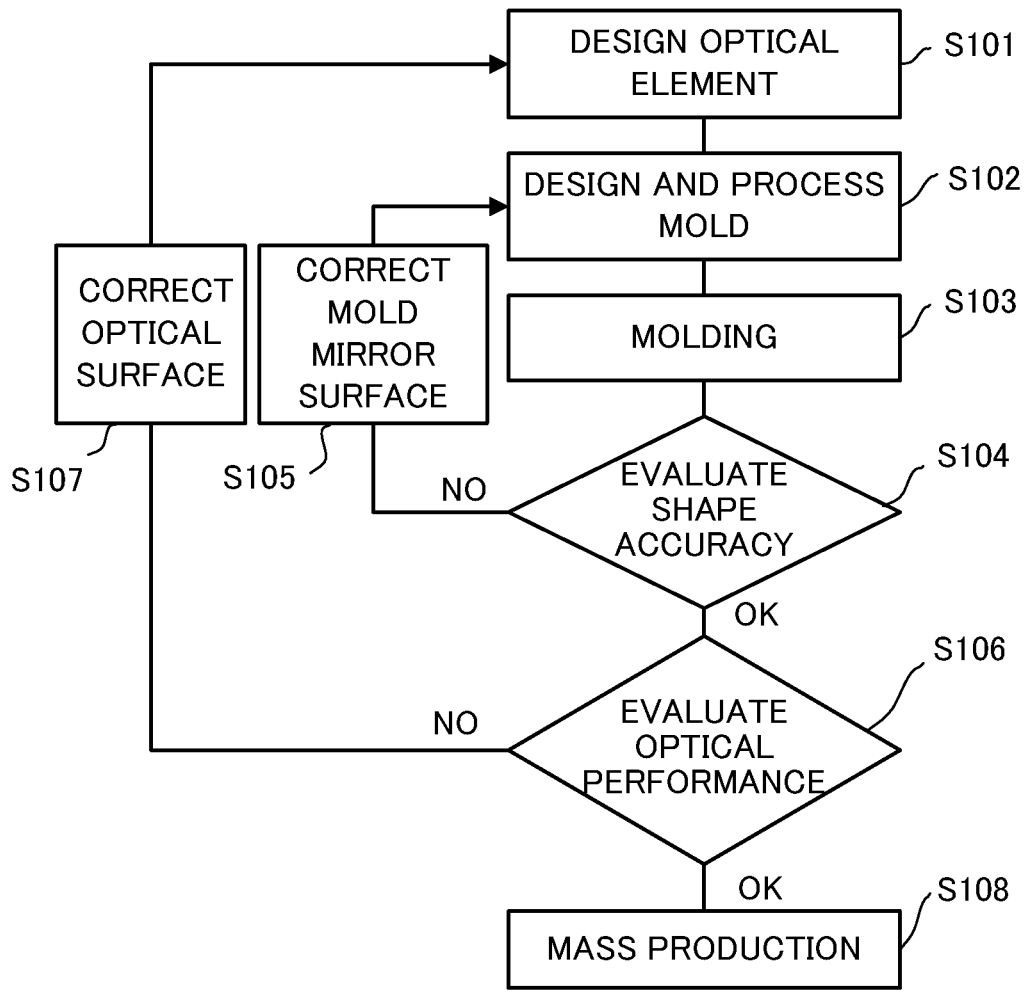
FIG. 8 shows an optical element manufacturing method that uses a refractive index distribution measurement method according to the present invention.

FIG. 8 is an illustrative manufacturing flow of an optical element that uses molding.

In FIG. 8, S101 denotes a step of designing an optical element, and a designer designs an optical element by using optical designing software or the like. S102 denotes a step of designing and working a mold configured to mold the optical element based on the optical element designed in the step S101. S103 denotes a step of molding the optical element by using the mold worked in the step S102.

S104 denotes a step of measuring a shape of the optical element molded in the step S103 and of evaluating its accuracy. If the shape evaluated in the step S104 does not meet the accuracy requirement, a correction amount of a mirror surface of the mold is calculated in a step S105. The mold is worked again in the step S102.

S106 denotes a step of evaluating the optical performance of the optical element that satisfies predetermined shape accuracy in the step S104. A calculation flow of a refractive index distribution similar to that described with reference to FIG. 3 is executed, and the optical performance of the optical element is evaluated by using its result in a step S106. If the optical performance evaluated in the step S106 is below the required specification, a correction amount of an optical surface is calculated in a step S107, and an optical element is designed again by using its result in the step S101.

In a step S108, an optical element is mass-produced under the manufacturing condition of the optical element that satisfies the predetermined optical performance in the step S106.

Since the optical element manufacturing method of this embodiment provides a highly accurate measurement of an internal refractive index distribution of the optical element, an optical element even made of a high refractive index glass material can be accurately mass-produced by molding.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-329274, filed Dec. 25, 2008, which is hereby incorporated by reference herein in its entirety.

What is claimed is:

1. A refractive index distribution measurement method comprising the steps of:
   measuring a first transmission wavefront of a test object by introducing reference light to the test object immersed in a first medium having a first refractive index lower than that of the test object by 0.01 or more;
   measuring a second transmission wavefront of the test object by introducing the reference light to the test object immersed in a second medium having a second refractive index lower than that of the test object by 0.01 or more and different from the first refractive index;
   calculating a first wavefront aberration, which a difference between the measured first transmission wavefront and a transmission wavefront of a reference object having a specific refractive index distribution when the reference object is located in the first medium;
   calculating a second wavefront aberration, which is a difference between the measured second transmission wavefront and a transmission wavefront of the reference object when the reference object is located in the second medium; and
   calculating a refractive index distribution of the test object by removing a shape component of the test object based on the calculated first and second wavefront aberrations.

2. The refractive index distribution measurement method according to claim 1, wherein the first transmission wavefront measuring step measures an amount corresponding to a gradient of a wavefront shape of the first transmission wavefront and the second transmission wavefront measuring step measures an amount corresponding to a gradient of a wavefront shape of the second transmission wavefront.

3. The refractive index distribution measurement method according to claim 1, wherein each of the first transmission wavefront measuring step and the second transmission wavefront measuring step uses a Talbot interferometer that includes a two-dimensional diffraction grating.

4. The refractive index distribution measurement method according to claim 1, wherein each of the first transmission wavefront measuring step and the second transmission wavefront measuring step uses a Shack-Hartmann sensor.

5. The refractive index distribution measurement method according to claim 1, wherein the first and second refractive indices are different from each other by 0.01 or more.

6. The refractive index distribution measurement method according to claim 1, wherein each of the first transmission wavefront measuring step and the second transmission wavefront measuring step maintains an equal inclination to the test object of a ray of the reference light passing through the test object.

7. A refractive index distribution measurement apparatus comprising:
   a light source;
   a pinhole configured to generate reference light with light from the light source;
   shearing interferometer configured to:
      measure a first transmission wavefront of a test object with the reference light from the pinhole introduced to the test object immersed in a first medium having a first refractive index lower than that of the test object by 0.01 or more; and
      measure a second transmission wavefront of the test object with the reference light introduced to the test object immersed in a second medium having a second refractive index lower than that of the test object by 0.01 or more and different from the first refractive index; and
   a microcomputer configured to:
      calculate a first wavefront aberration, which is a difference between the measured first transmission wavefront and a transmission wavefront of a reference object having a specific refractive index distribution when the reference object is located in the first medium;
      calculate a second wavefront aberration, which is a difference between the measured second transmission wavefront and a transmission wavefront of the reference object when the reference object is located in the second medium; and
      calculate a refractive index distribution of the test object by removing a shape component of the test object based on the calculated first and second wavefront aberrations.

8. The refractive index distribution measurement apparatus according to claim 7, wherein the test object is an optical element, and the test object and each of the pinhole and the shearing interferometer are configured to move relative to each other in an optical axis direction of the test object.

9. A method of manufacturing an optical element, the method comprising the steps of:
   molding the optical element; and
   evaluating a molded optical element using a refractive index distribution measurement method,
   wherein the refractive index distribution measurement method includes the steps of:
   measuring a first transmission wavefront of a test object by introducing reference light to the test object immersed in a first medium having a first refractive index lower than that of the test object by 0.01 or more;
   measuring a second transmission wavefront of the test object by introducing the reference light to the test object immersed in a second medium having a second refractive index lower than that of the test object by 0.01 or more and different from the first refractive index;
   calculating a first wavefront aberration, which a difference between the measured first transmission wavefront and a transmission wavefront of a reference object having a specific refractive index distribution when the reference object is located in the first medium;
   calculating a second wavefront aberration, which is a difference between the measured second transmission wavefront and a transmission wavefront of the reference object when the reference object is located in the second medium; and calculating a refractive index distribution of the test object by removing a shape component of the test object based on the calculated first and second wavefront aberrations.

10. A refractive index distribution measurement method comprising the steps of:
    measuring a first transmission wavefront of a test object by introducing reference light to the test object immersed in a first medium having a first refractive index lower than that of the test object;
    measuring a second transmission wavefront of the test object by introducing the reference light to the test object immersed in a second medium having a second refractive index lower than that of the test object and different from the first refractive index;
    calculating a first wavefront aberration, which a difference between the measured first transmission wavefront and a transmission wavefront of a reference object having a specific refractive index distribution when the reference object is located in the first medium;
    calculating a second wavefront aberration, which is a difference between the measured second transmission wavefront and a transmission wavefront of the reference object when the reference object is located in the second medium; and
    calculating a refractive index distribution of the test object by removing a shape component of the test object based on the calculated first and second wavefront aberrations.

11. A refractive index distribution measurement method comprising the steps of:
    measuring a first transmission wavefront of a test object by introducing reference light to the test object immersed in a first medium having a first refractive index lower than that of the test object, using a shearing interferometer;
    measuring a second transmission wavefront of the test object by introducing the reference light to the test object immersed in a second medium having a second refractive index lower than that of the test object and different from the first refractive index, using the shearing interferometer;
    calculating a first wavefront aberration, which a difference between the measured first transmission wavefront and a transmission wavefront of a reference object having a specific refractive index distribution when the reference object is located in the first medium;
    calculating a second wavefront aberration, which is a difference between the measured second transmission wavefront and a transmission wavefront of the reference object when the reference object is located in the second medium; and
    calculating a refractive index distribution of the test object by removing a shape component of the test object based on the calculated first and second wavefront aberrations.

12. A refractive index distribution measurement method comprising the steps of:
    measuring a first transmission wavefront of a test object by introducing reference light to the test object immersed in a first medium having a first refractive index lower than that of the test object, using one of a Shack-Hartmann method, a Hartmann method, or a Ronchi testing method;
    measuring a second transmission wavefront of the test object by introducing the reference light to the test object immersed in a second medium having a second refractive index lower than that of the test object and different from the first refractive index, using the one of the Shack-Hartmann method, the Hartmann method, or the Ronchi testing method; and
    calculating a first wavefront aberration, which a difference between the measured first transmission wavefront and a transmission wavefront of a reference object having a specific refractive index distribution when the reference object is located in the first medium;
    calculating a second wavefront aberration, which is a difference between the measured second transmission wavefront and a transmission wavefront of the reference object when the reference object is located in the second medium; and
    calculating a refractive index distribution of the test object by removing a shape component of the test object based on the calculated first and second wavefront aberrations.

13. A refractive index distribution measurement apparatus comprising:
    a light source;
    a pinhole configured to generate reference light with light from the light source;
    a wavefront measurement sensor configured to:
        measure a first transmission wavefront of a test object with the reference light from the pinhole introduced to the test object immersed in a first medium having a first refractive index lower than that of the test object by 0.01 or more; and
        measure a second transmission wavefront of the test object with the reference light introduced to the test object immersed in a second medium having a second refractive index lower than that of the test object by 0.01 or more and different from the first refractive index; and
    a microcomputer configured to:
        calculate a first wavefront aberration, which is a difference between the measured first transmission wavefront and a transmission wavefront of a reference object having a specific refractive index distribution when the reference object is located in the first medium;
        calculate a second wavefront aberration, which is a difference between the measured second transmission wavefront and a transmission wavefront of the reference object when the reference object is located in the second medium; and
        calculate a refractive index distribution of the test object by removing a shape component of the test object based on the calculated first and second wavefront aberrations.

14. The refractive index distribution measurement apparatus according to claim 13, wherein the test object is an optical element, and the test object and each of the pinhole and the wavefront measurement sensor are configured to move relative to each other in an optical axis direction of the test object.

* * * * *